United States Patent [19]
Chen et al.

[11] Patent Number: 5,773,644
[45] Date of Patent: Jun. 30, 1998

[54] CYCLOPROPYL ALKANOIC ACID DERIVATIVES

[75] Inventors: Barbara B. Chen, Glenview, Ill.;
Helen Y. Chen, Livingston, N.J.;
Michael Clare, Skokie, Ill.;
Shashidhar N. Rao, Mundelein, Ill.;
Mark A. Russell, Gurnee, Ill.

[73] Assignee: G. D. Searle & Co., Chicago, Ill.

[21] Appl. No.: 825,040

[22] Filed: Mar. 27, 1997

Related U.S. Application Data

[60] Provisional application No. 60/014,411 Mar. 29, 1996.
[51] Int. Cl.⁶ ............... C07C 241/00; C07C 229/00; C07D 239/00
[52] U.S. Cl. ............... 562/439; 560/34; 544/246
[58] Field of Search ............... 560/34; 562/439; 544/246

[56] References Cited

U.S. PATENT DOCUMENTS 5,523,302  6/1996  Cain et al. ............... 514/252

FOREIGN PATENT DOCUMENTS

| | | | |
|---|---|---|---|
| 0 478 328 A1 | 4/1992 | European Pat. Off. | C07C 271/22 |
| 0 478 363 A2 | 4/1992 | European Pat. Off. | C07D 211/22 |
| WO 95/32710 | 12/1995 | WIPO | A61K 31/18 |

*Primary Examiner*—Gary Geist
*Assistant Examiner*—Brian J. Davis
*Attorney, Agent, or Firm*—Cynthia S. Kovacevic

[57] ABSTRACT

The present invention relates to a class of compounds represented by the Formula I

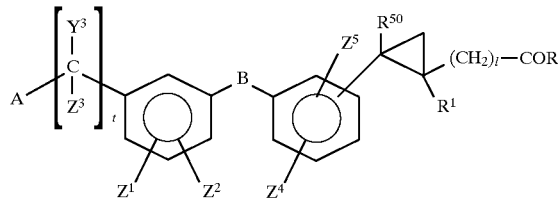

or a pharmaceutically acceptable salt thereof, pharmaceutical compositions comprising compounds of the Formula I, and methods of selectively inhibiting or antagonizing the $\alpha_v\beta_3$ integrin.

31 Claims, No Drawings

CYCLOPROPYL ALKANOIC ACID DERIVATIVES

FIELD OF THE INVENTION

The present invention relates to pharmaceutical agents (compounds) which are useful as $\alpha_v\beta_3$ integrin antagonists or inhibitors and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various $\alpha$ subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy (Adonis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic targets for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9) (1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention relates to a class of compounds represented by the Formula I

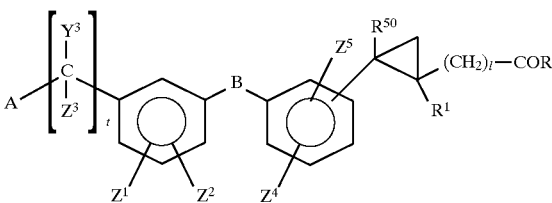

or a pharmaceutically acceptable salt thereof, wherein

A is

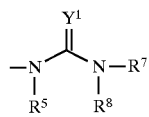

wherein $Y^1$ is selected from the group consisting of $N-R^2$, O, and S;

$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy and phenyl;

or $R^2$ taken together with $R^7$ forms a 5 membered heteroaromatic ring;

or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; $-SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl; or A is

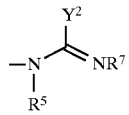

wherein $Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; $-S-R^9$ and $-O-R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above;

or $Y^2$ (when $Y^2$ is carbon) taken together with $R^7$ forms a 4–12 membered mononitrogen containing ring optionally substituted with alkyl, aryl or hydroxy;

$Z^1$, $Z^2$, $Z^4$ and $Z^5$ are independently selected from the group consisting of H; alkyl; hydroxy; alkoxy; aryloxy; arylalkyloxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of $-CH_2CONH-$, $-CONH-(CH_2)p-$, $-CONR^{11}-$, —NHCO—(CH$_2$)$_n$—, —C(O)O—, and —SO$_2$NH—, wherein p is an integer selected from the group consisting of 0, 1 and 2; wherein R$^{11}$ is selected from the group consisting of H, alkyl, alkenyl, alkynyl, benzyl and phenethyl; wherein n is an integer selected from the group consisting of 0, 1, 2 and 3;

l is an integer 0, 1, 2, or 3;

t is an integer 0, 1 or 2;

R$^{50}$ is selected from the group consisting of H, alkyl and aryl;

R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof;

Y$^3$ and Z$^3$ are independently selected from the group consisting of H, alkyl, aryl, cycloalkyl and aralkyl;

R$^1$ is selected from the group consisting of hydrogen; alkyl; amino,

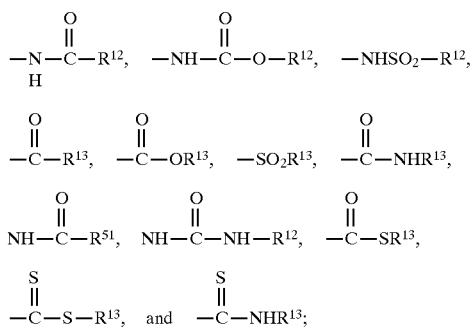

R$^{12}$ is selected from the group consisting of H, alkyl, cycloalkyl, alkylaryl and aryl;

R$^{51}$ is selected from the group consisting of N-substituted pyrrolidinyl, piperidinyl and morpholinyl;

R$^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

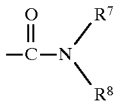

wherein R$^7$ and R$^8$ are as defined above and provided that taken together with the nitrogen, R$^7$ and R$^8$ comprise an amino acid.

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A preferred embodiment of the present invention is a compound of the Formula II

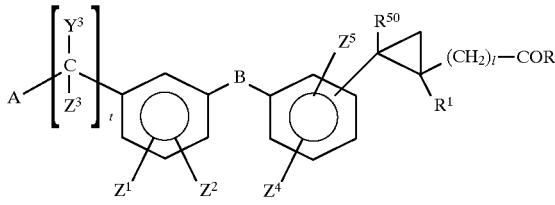

Another preferred embodiment of the present invention is a compound of the Formula III

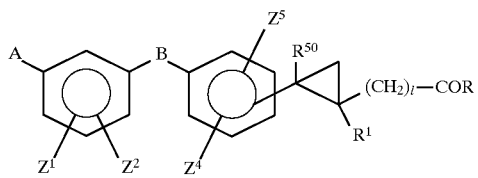

Another preferred embodiment of the present invention is a compound of the Formula IV

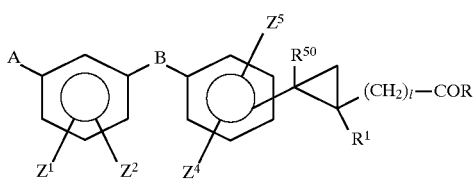

Another preferred embodiment of the present invention is a compound of the Formula V

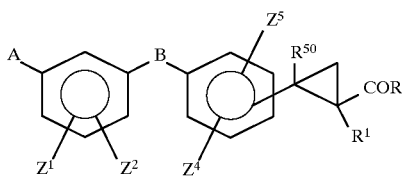

The invention further relates to pharmaceutical compositions containing therapeutically effective amounts of the compounds of Formulas I–V.

The invention also relates to a method of selectively inhibiting or antagonizing the $\alpha_v\beta_3$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, smooth muscle cell migration and restenosis by administering a therapeutically effective amount of a compound of the Formula I–V to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula

As used herein, the term "N-substituted pyrrolidinyl" refers to a radical of the formula

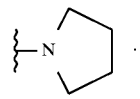

As used herein the term "N-substituted piperidinyl" refers to a radical of the formula

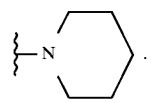

The term "morpholinyl as used herein refers to a radical of the formula

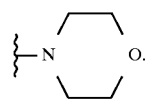

The terms "hydroxy" and "hydroxyl" as used herein are synonymous and are represented by a radical of the formula

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula —$OR^{20}$, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

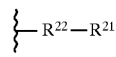

wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "aralkyloxy" or "arylalkyloxy" refers to a radical of the formula

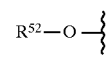

wherein $R^{52}$ is "arylalkyl" as defined above.

As used herein the term "nitro" is represented by a radical of the formula

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl derivative" refers to a radical of the formula

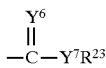

wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula —$NH_2$.

As used herein the term "alkylsulfonyl" or "alkylsulfone" refers to a radical of the formula

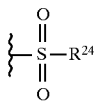

wherein $R^{24}$ is alkyl as defined above.

As used herein the term "alkylthio" refers to a radical of the formula —$SR^{24}$ wherein $R^{24}$ is alkyl as defined above.

As used herein the term "sulfonic acid" refers to a radical of the formula

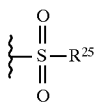

wherein $R^{25}$ is H, alkyl or aryl as defined above.

As used herein the term "sulfonamide" refers to a radical of the formula

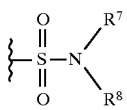

wherein $R^7$ and $R^8$ are as defined above.

As used herein the term "fused aryl" refers to an aromatic ring such as the aryl groups defined above fused to one or more phenyl rings. Embraced by the term "fused aryl" is the radical naphthyl.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

and the term "ethylenedioxy" refers to the radical

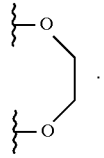

As used herein the term "4–12 membered dinitrogen containing heterocycle refers to a radical of the formula

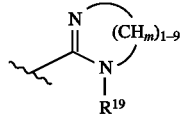

wherein m is 1 or 2 and $R^{19}$ is H, alkyl, aryl, or aralkyl and more preferably refers to 4–9 membered ring and includes rings such as imidazoline.

As used herein the term "5-membered heteroaromatic ring" includes for example a radical of the formula

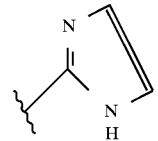

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

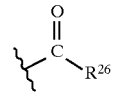

wherein $R^{26}$ is alkyl, alkenyl, alkynyl, aryl or aralkyl as defined above. Encompassed by such radical are the groups acetyl, benzoyl and the like.

As used herein the term "thio" refers to a radical of the formula

As used herein the term "sulfonyl" refers to a radical of the formula

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

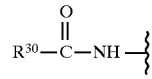

wherein $R^{30}$ is alkyl, aralkyl or aryl as defined above.

As used herein the term "amido" refers to a radical of the formula

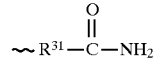

wherein $R^{31}$ is a bond or alkylene as defined above.

As used herein the term "alkylamino" refers to a radical of the formula —$NHR^{32}$ wherein $R^{32}$ is alkyl as defined above.

As used herein the term "dialkylamino" refers to a radical of the formula —$NR^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

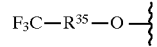

wherein $R^{35}$ is a bond or an alkylene as defined above.

As used herein the term "alkylaminosulfonyl" refers to a radical of the formula

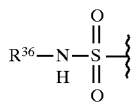

wherein $R^{36}$ is alkyl as defined above.

As used herein the term "alkylsulfonylamino" refers to a radical of the formula

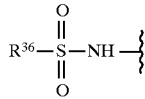

wherein $R^{36}$ is alkyl as defined above.

As used herein the term "trifluoromethylthio" refers to a radical of the formula

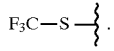

As used herein the term "trifluoromethylsulfonyl" refers to a radical of the formula

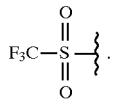

As used herein the term "4–12 membered mononitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

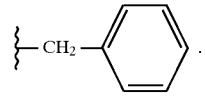

As used herein the term "phenethyl" refers to the radical

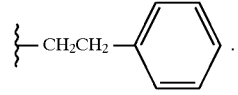

As used herein the term "4–12 membered mononitrogen containing sulfur or oxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

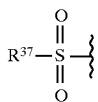

wherein $R^{37}$ is aryl as defined above.

As used herein the terms "alkylsulfoxide" or "arylsulfoxide" refer to radicals of the formula

wherein $R^{38}$ is, respectively, alkyl or aryl as defined above.

As used herein the term "phosphonic acid derivative" refers to a radical of the formula

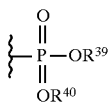

wherein $R^{39}$ and $R^{40}$ are the same or different H, alkyl, aryl or aralkyl.

As used herein the term "phosphinic acid derivatives" refers to a radical of the formula

wherein $R^{41}$ is H, alkyl, aryl or aralkyl as defined above.

As used herein the term "arylthio" refers to a radical of the formula

wherein $R^{42}$ is aryl as defined above.

As used herein the term "monocyclic heterocycle thio" refers to a radical of the formula

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

wherein $R^{43}$ is a monocyclic heterocycle radical as defined above.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR = proton nuclear magnetic resonance
AcOH = acetic acid
BH$_3$-THF = borane-tetrahydrofuran complex
BOC = tert-butoxycarbonyl
Cat. = catalytic amount
CH$_2$Cl$_2$ = dichloromethane
CH$_3$CN = acetonitrile
CH$_3$I = iodomethane
CHN analysis = carbon/hydrogen/nitrogen elemental analysis
CHNCl analysis = carbon/hydrogen/nitrogen/chlorine elemental analysis
CHNS analysis = carbon/hydrogen/nitrogen/sulfur elemental analysis
DCC = 1,3-dicyclohexylcarbodiimide
DIEA = diisopropylethylamine
DMA = N,N-dimethylacetamide
DMAP = 4-(N,N-dimethylamino) pyridine
DMF = N,N-dimethylformamide
DSC = disuccinyl carbonate
EDCl = 1-(3-dimethylaminopropyl)-3-ethylcarbodiimide hydrochloride
Et$_2$O = diethyl ether
Et$_3$N = triethylamine
EtOAc = ethyl acetate
EtOH = ethanol
FAB MS = fast atom bombardment mass spectroscopy
g = gram(s)
GIHA HCl = meta-guanidino-hippuric acid hydrochloride
GIHA = meta-guanidino-hippuric acid
HPLC = high performance liquid chromatography
IBCF = isobutylchloroformate
K$_2$CO$_3$ = potassium carbonate
KOH = potassium hydroxide
LiOH = lithium hydroxide
MCPBA = m-chloroperoxybenzoic acid or m-chloroperbenzoic acid
MeOH = methanol
MesCl = methanesulfonylchloride
mg = milligram
MgSO$_4$ = magnesium sulfate
ml = milliliter
mL = milliliter
MS = mass spectroscopy
N$_2$ = nitrogen
NaCNBH$_3$ = sodium cyanoborohydride
Na$_3$PO$_4$ = sodium phosphate
Na$_2$SO$_4$ = sodium sulfate
NaHCO$_3$ = sodium bicarbonate
NaOH = sodium hydroxide
NH$_4$HCO$_3$ = ammonium bicarbonate
NH$_4{}^+$HCO$_2{}^-$ = ammonium formate
NMM = N-methyl morpholine
NMR = nuclear magnetic resonance
RPHPLC = reverse phase high performance liquid chromatography
RT = room temperature
KSCN = potassium thiocyanate
Pd/C = palladium on carbon
Bn = benzyl
Et = ethyl
Me = methyl
Ph = phenyl
NEt$_3$ = triethylamine
t-BOC = tert-butoxycarbonyl
TFA = trifluoroacetic acid
THF = tetrahydrofuran
Δ = heating the reaction mixture As used herein HPLC-Method 1 refers to reverse phase C-18 functionalized silica gel column (50×300 mm) using a linear gradient of 95% 0.6% TFA/water:5% CH$_3$CN to 60% 0.6% TFA/water: 40% CH$_3$CN with a flow rate of 80 ml/minute.

The compounds as shown in Formulas I–V can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J Pharm. Sci.*, 66(1), 1–19 (1977) for additional examples of pharmaceutically acceptable salts.)

For the selective inhibition or antagonism of $\alpha_v\beta_3$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ cell surface receptor which method comprises administering a therapeutically effective amount of a compound selected from the class of compounds depicted in Formulas I–V, wherein one or more compounds of the Formulas I–V is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_v\beta_3$ cell surface receptor. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 1000 mg/kg of body weight per day are useful in the treatment of the above-indicated conditions and more preferably 0.01 mg to about 100 mg/kg of body weight.

The active ingredient administered by injection is formulated as a composition wherein, for example, saline, dextrose or water may be used as a suitable carrier. A suitable daily dose would typically be about 0.01 to 10 mg/kg body weight injected per day in multiple doses depending on the factors listed above.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes I–III. Both an explanation of, and the actual procedures for, the various aspects of the present invention are described where appropriate. The following Schemes and Examples are intended to be merely illustrative of the present invention, and not limiting thereof in either scope or spirit. Those of skill in the art will readily understand that known variations of the conditions and processes described in the Schemes and Examples can be used to perform the process of the present invention.

Unless otherwise indicated all starting materials and equipment employed were commercially available.

SCHEME I
(A)
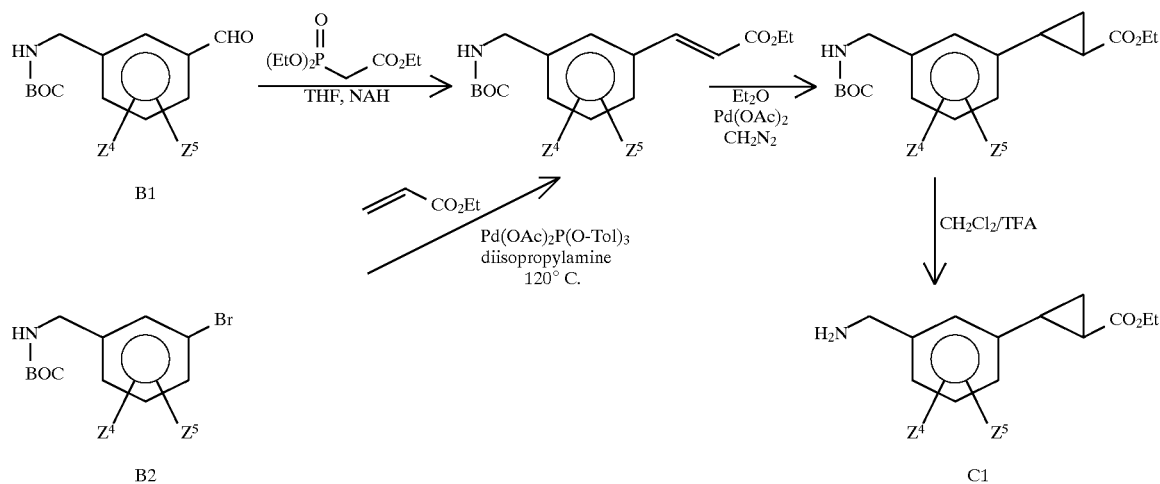
(B)
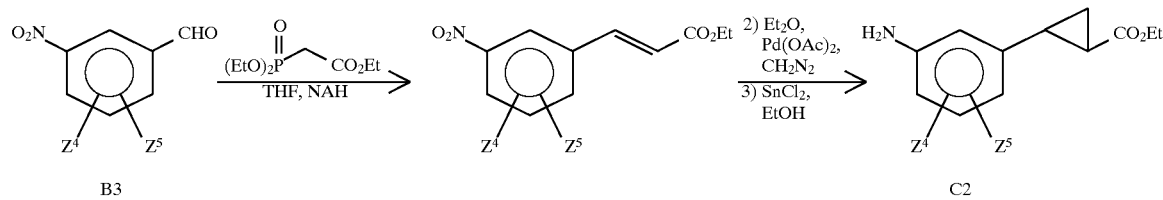
(C)
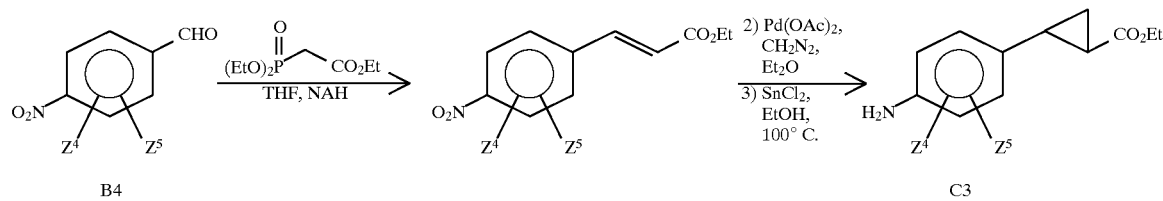
(D)
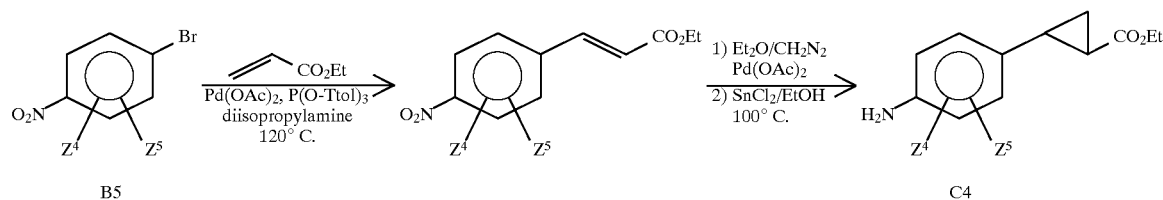
(E)
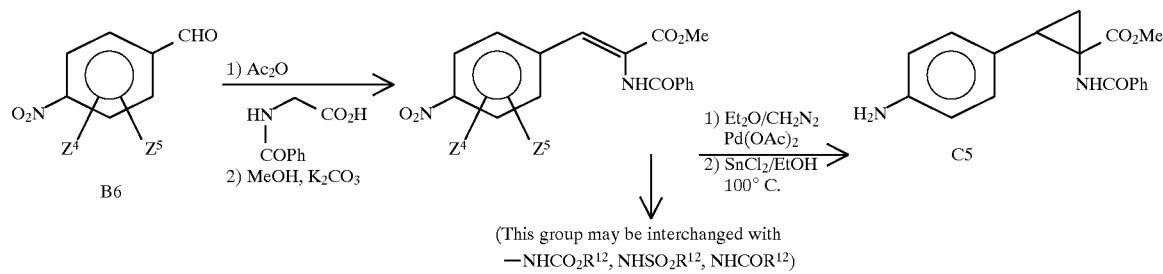

-continued
SCHEME I (F)
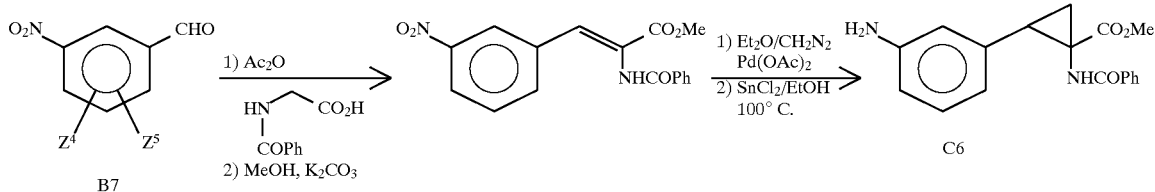

(G)
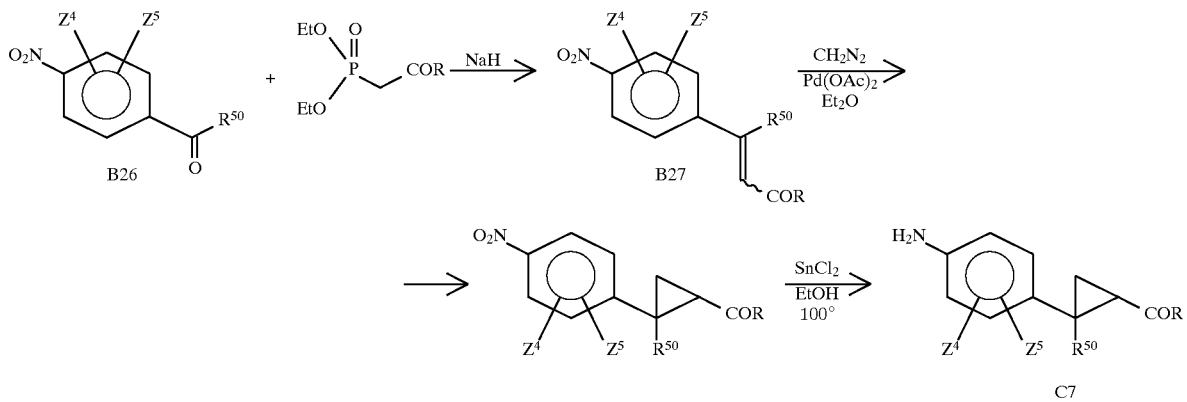

(H)
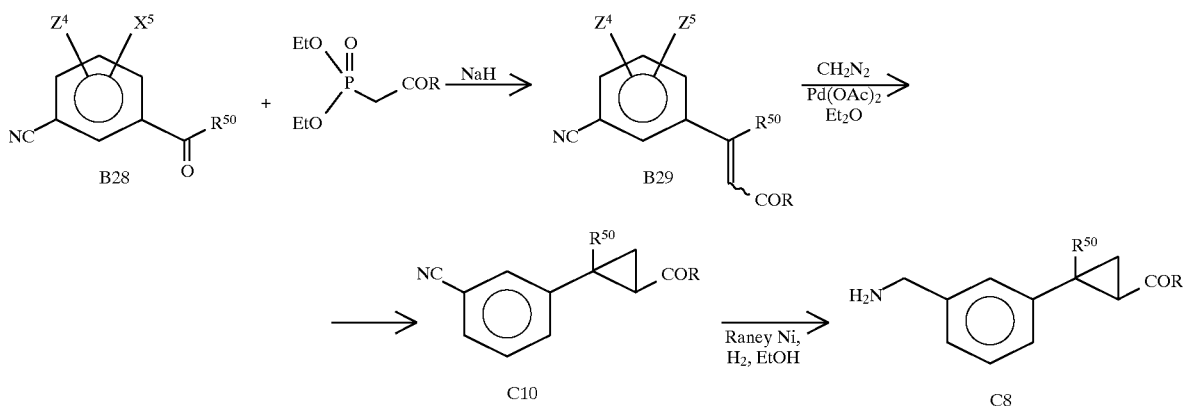

Schemes I–III are illustrative of methodology useful for preparing various compounds of the present invention. Such methodology is more specifically defined in the examples which follow. Such methodology can be modified by one skilled in the art, substituting known reagents and conditions from conventional methodology to produce the desired compounds.

In Scheme I(A) cyclopropane C1 is readily prepared from either aldehydes B1 or bromides B2.

Aldehyde B1 is condensed with $(EtO)_2P(O)CH_2CO_2Et$ under standard conditions (NaH/THF, 0° to room temperature). The resulting cinnamic acid derivative can be cyclopropanated ($Pd(OAc)_2$, $Et_2O$, $CH_2N_2$; see example 1B) and then deprotected (TFA, $CH_2Cl_2$, 0° C.) to afford the desired cyclopropane C1.

In a complimentary procedure, bromide B2 can be coupled with ethyl acrylate ($Pd(OAc)_2$, P(O-Tol)$_3$ i-Pr$_2$NH, 120°) to afford the above mentioned cinnamic acid analog. Cyclopropanation, followed by deprotection affords cyclopropane C1 as described above.

In Scheme I(B) cyclopropane C2 is readily prepared from aldehyde B3.

Aldehyde B3 is condensed with $(EtO)_2P(O)CH_2CO_2Et$ under standard conditions (NaH, THF, 0° to room temperature.) The resulting nitrophenylcinnamic acid derivative can by cyclopropanated ($Pd(OAc)_2$, $Et_2O$, $CH_2N_2$) and then the nitro functionality can be reduced ($SnCl_2$, $Et_2O$, EtOH, 100°) to afford cyclopropane C2.

In Scheme I(C) cyclopropane C3 is readily prepared from aldehyde B4 using the reaction conditions described in Scheme I(B).

In Scheme I(D) cyclopropane C4 can be prepared from bromide B5.

Bromide B5 can be coupled with alkyl acrylates using a standard Heck coupling procedure ($Pd(OAc)_2$, P(O-Tol)$_3$ i-Pr$_2$NH, 120°) to afford a nitrocinnamic acid analog. Cyclopropanation of the nitrocinnamic acid analog ($Pd(OAc)_2$, $Et_2O$, $CH_2N_2$) followed by reduction ($SnCl_2$, $2H_2O$, EtOH, 100°) affords the cyclopropane C4.

In Scheme I(E) cyclopropane C5 can be prepared from aldehyde B6 as described below.

Aldehyde B6 is condensed with N-benzoylglycine (Ac$_2$O, 100°) and the resulting azalactone is hydrolysed (MeOH/ K$_2$CO$_3$) to afford the corresponding dehydroamino acid analog. Cyclopropanation of the dehydroamino acid analog, followed by tin II chloride reduction would afford cyclopropane C5.

In Scheme I(F) in an analogous fashion to that described in Scheme I(E), aldehyde B7 can be converted into cyclopropane C6.

In Scheme I(G) in an analogous fashion to that described in Scheme I(B), aldehydes or ketones B26 can be converted into cyclopropane C7.

In Scheme I(H) cyclopropane C8 can be prepared from aldehyde or ketone B28 as described below.

Aldehyde/or ketone B28 is condensed with (Eto)$_2$P(O) CH$_2$CO$_2$Et under standard conditions (NaH, THF, 0° to room temperature.) The resulting cyanophenyl cinnamic acid derivative can be cyclopropanated (Pd(OAc)$_2$, Et$_2$O, CH$_2$N$_2$) and then reduced (Raney Ni, EtOH, 60 psi) to afford cyclopropane C8.

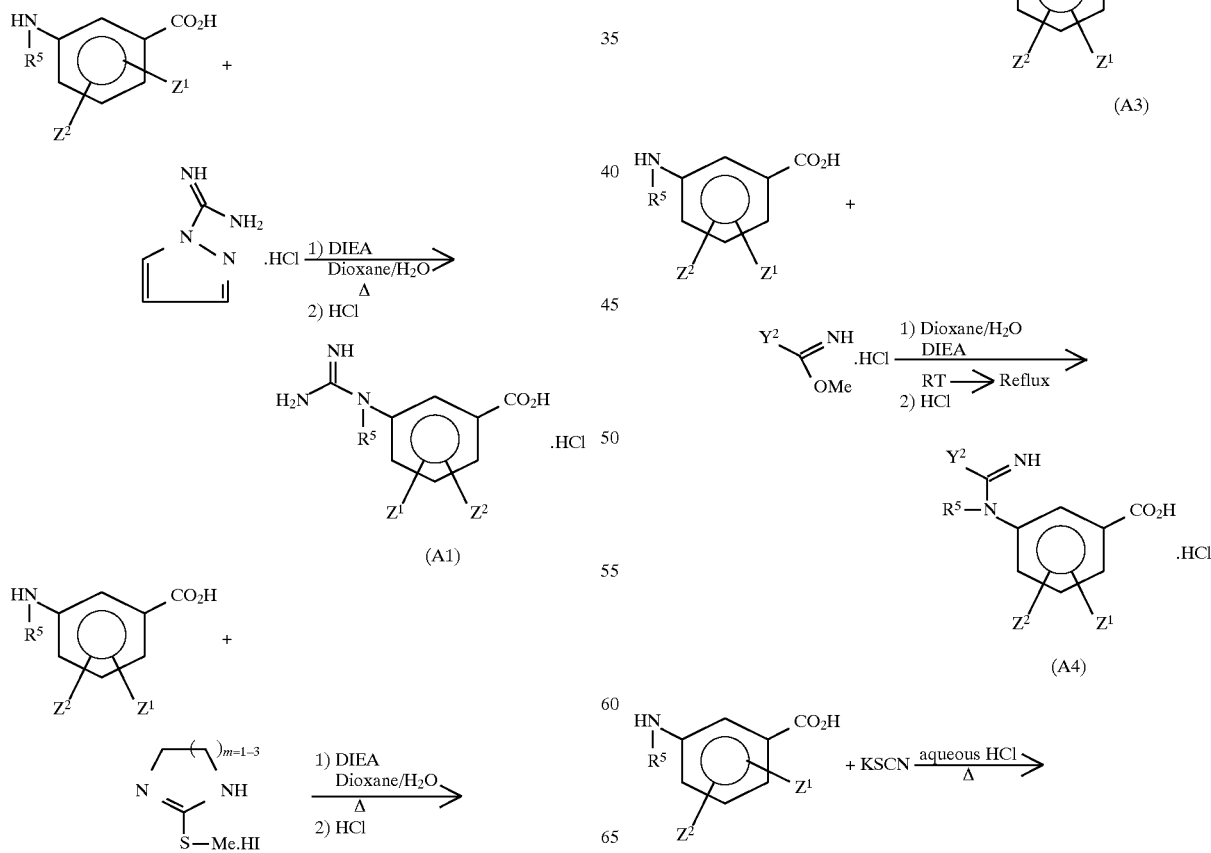

-continued
SCHEME II
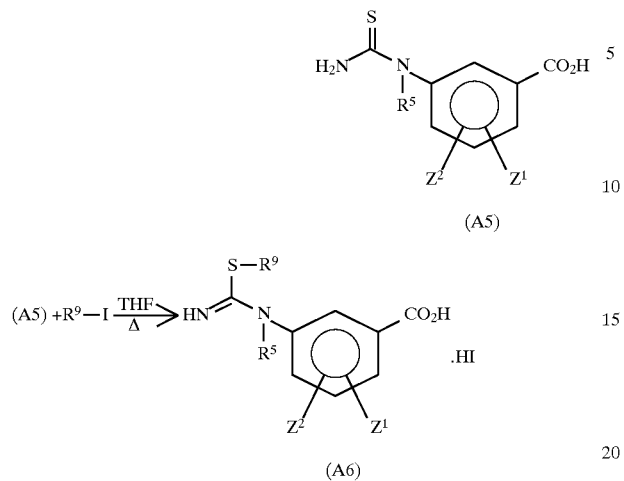
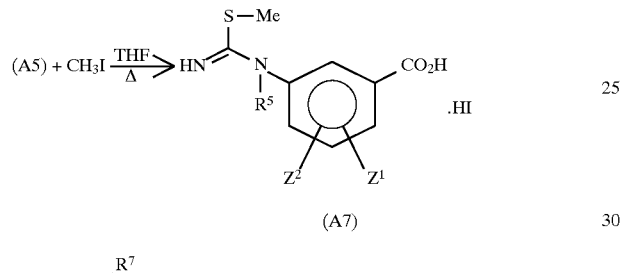
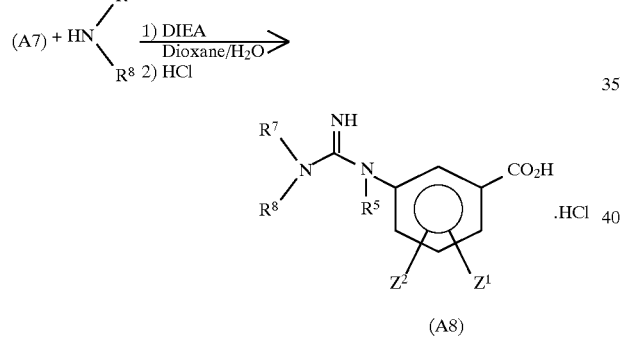
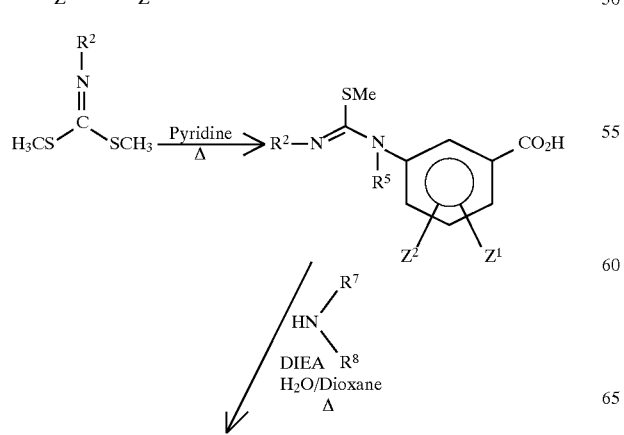
-continued
SCHEME II
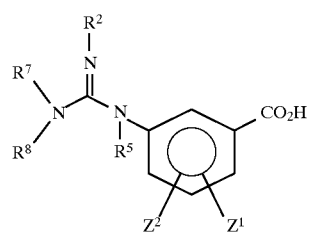
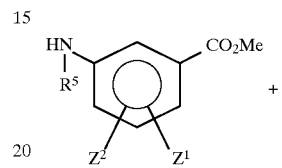
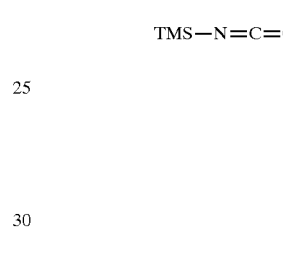
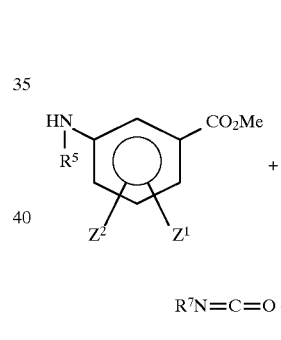

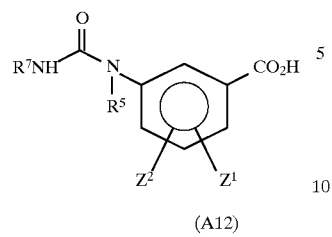
(A12)
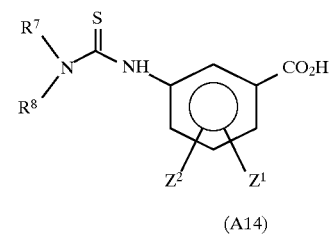
(A14)
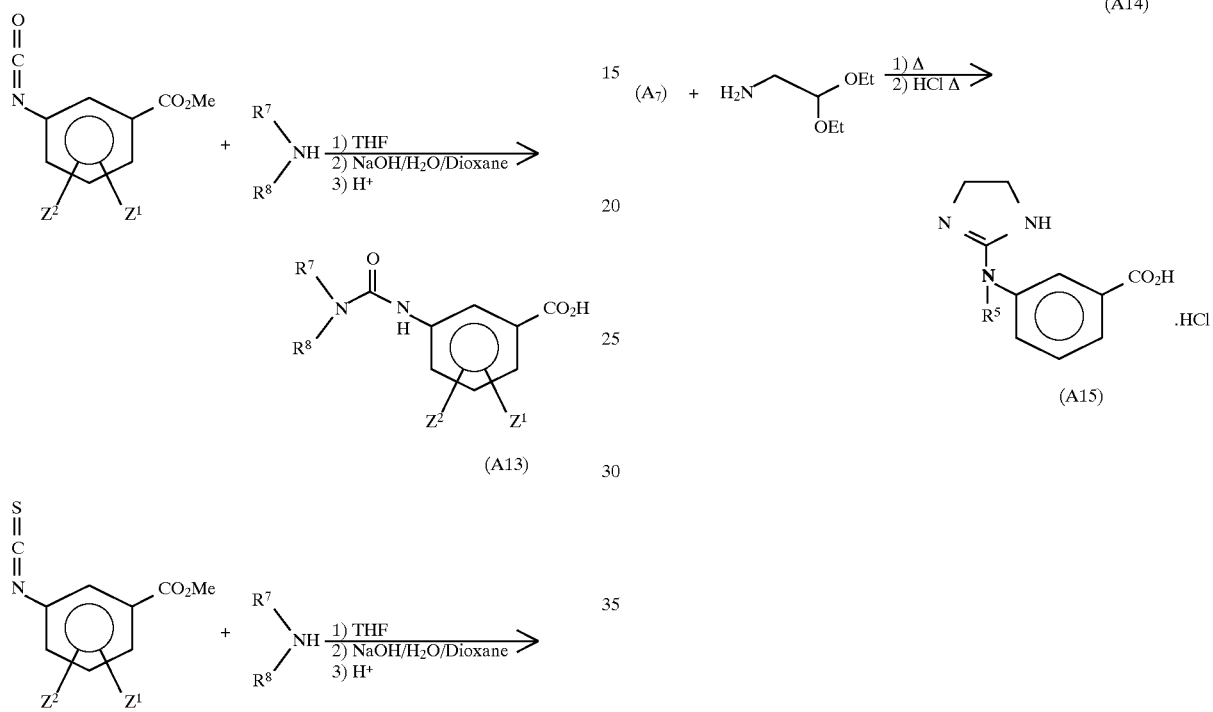
(A13)
(A15)
SCHEME III
Method A
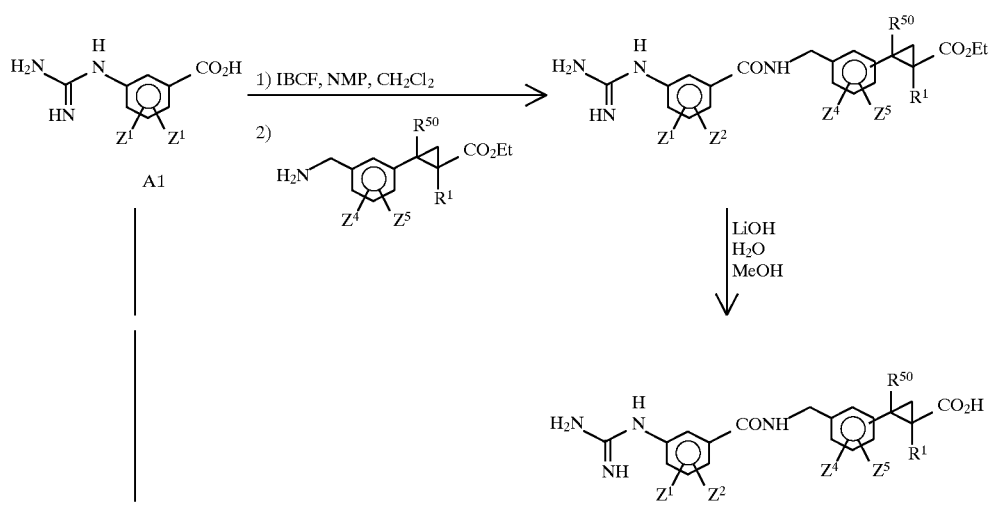

-continued
SCHEME III

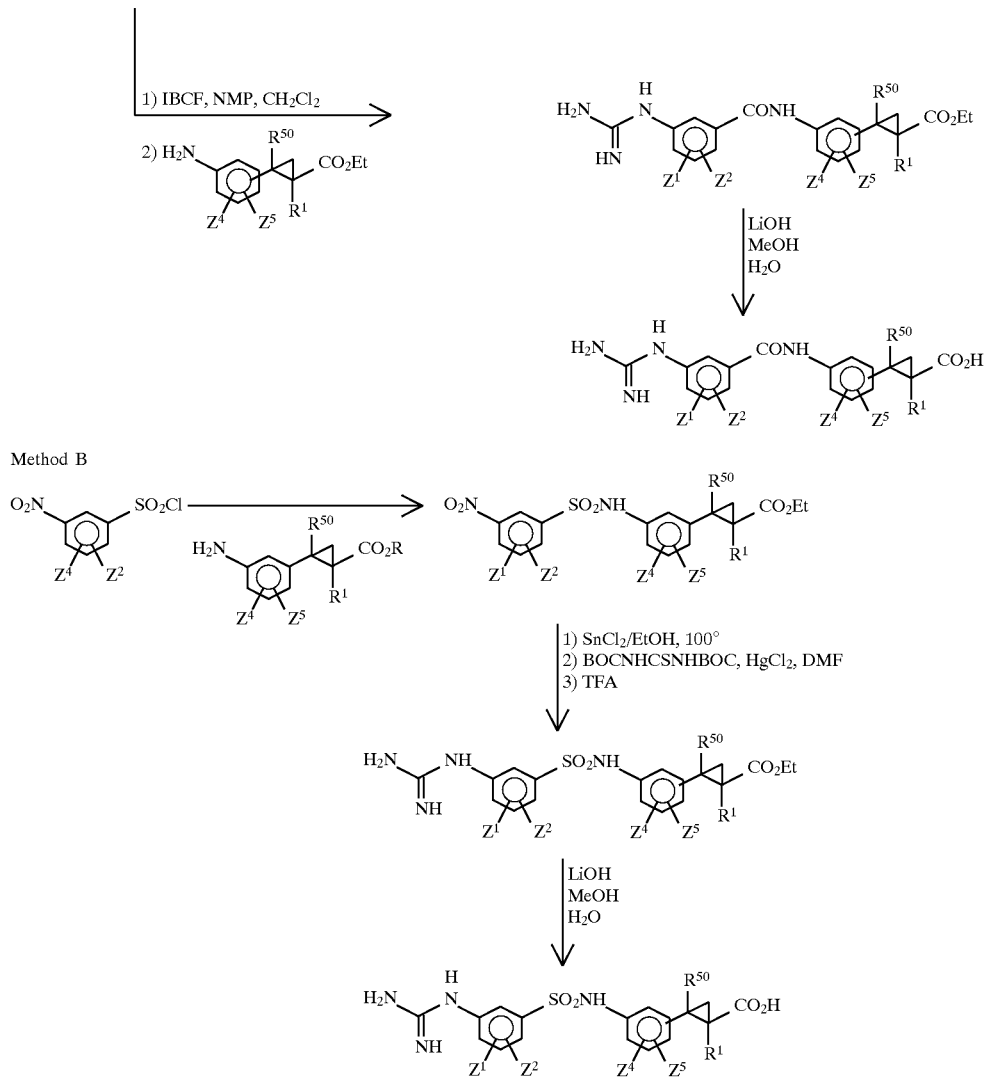

In Scheme II:

In the synthesis of intermediate benzoic acids (A1) through (A15), the starting amino benzoic acids

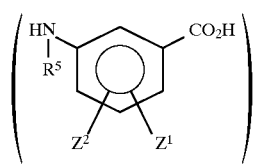

are either commercially available or can be converted to such amino benzoic acids via reduction of the corresponding nitro benzoic acid, which can be obtained commercially or synthesized by nitration of the appropriate benzoic acid, followed by reduction to the desired amino benzoic acid. These are all when $R^5$ is H. If $R^5$ is other than H, alkylation of the amino functionality can be achieved by conventional methodology.

Furthermore, synthesis of intermediate (A2) can also be accomplished as disclosed generally in U.S. Pat. No. 3,202,660, starting with the appropriate amino benzoic acid.

Furthermore, intermediate (A2) and (A15) as well as further analogues of (A2) and (A15) such as substitutions on the heterocyclic ring, oxazolidines, thiazolidines, benzimidazoles and the like can also be accomplished as disclosed in 1) Chem. Pharm. Bull. 41(1) 117–125 (1993)

2) Chem. Pharm. Bull. 33(10) 4409–4421 (1985)

3) J. Med. Chem. 18 (1), 90–99 (1975).

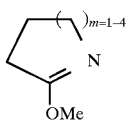

used in the synthesis of intermediates (A3), can be synthesized from

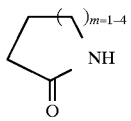

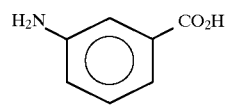

and $(Me)_3OBF_4$ in dichloromethane.

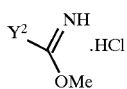

used in the synthesis of intermediate (A4), can be synthesized from $Y^2$—CN and MeOH (1 equivalent) and HCl gas (1 equivalent) in heptane.

SCHEME IV

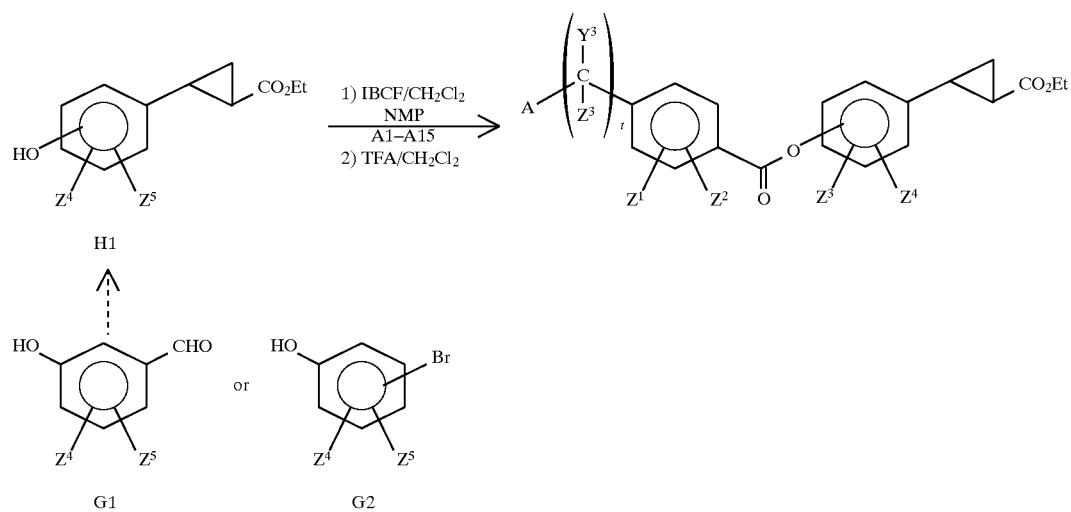

All other reagents in Scheme II are either commercially available or readily synthesized by methodologies known by those skilled in the art.

Coupling of the intermediates from Scheme II [(A1) through (A15)] with the intermediates (C1–C8) from Scheme I can be accomplished using coupling reagents known to those in the art and as depicted in Scheme III. When $R^{11}$ is not H, the appropriate nitrogen can be alkylated in an appropriate step by methodology known to those skilled in the art. Alternate acid derivatives R are synthesized by methodologies known to those skilled in the art.

To synthesize compounds wherein

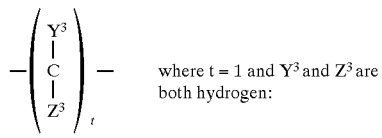

where t = 1 and $Y^3$ and $Z^3$ are both hydrogen:

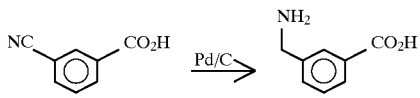

which is then treated in the same manner of further derivatization as exemplified in the previous schemes for:

In an analogous fashion to that described in Scheme II(a–h) and as depicted in Scheme IV, aldehyde G1 or bromide G2 can be converted into cyclopropane H1 (using well established and known chemistry to mask and unmask the hydroxy moiety).

Cyclopropane G2 is then readily coupled to benzoic acids A1–A15 using procedures previously described to afford the compounds of the present invention.

EXAMPLE A (3-Guanidinobenzoic acid hydrochloride)

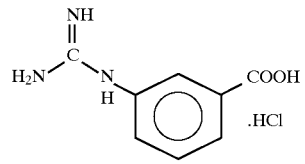

To 3,5-dimethylpyrazole-1-carboxamidine nitrate (6 g, 0.03 mole) (Aldrich) and diisopropylamine (3.8 g, 0.03 mole) in dioxane (20 ml) and $H_2O$ (10 ml) was added 3-aminobenzoic acid (2.7 g, 0.02 mole). The reaction was stirred at reflux for 2.5 hours then overnight at room temperature. The resulting precipitate was filtered, washed with dioxane/H₂O and dried. The precipitate was then slurried in H₂O and acidified with concentrated HCl until a solution formed. The solvent was removed under vacuum and the residue was slurried twice in ether (ether decanted off). The product was dried under vacuum to yield 3-guanidinobenzoic acid hydrochloride (1.77 g) as a white solid. MS and NMR were consistent with the desired structure.

EXAMPLE B 3-(1-Aza-2-amino-1-cycloheptyl)benzoic acid hydrochloride

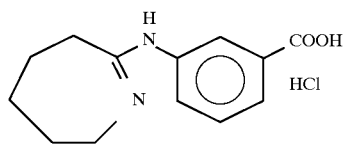

To 1-aza-2-methoxy-1-cycloheptene (3.67 g, 0.0288 mole) (Aldrich) in absolute ethanol (20 ml) was added 3-aminobenzoic acid hydrochloride (5 g, 0.0288 mole). A solution quickly formed. The reaction mixture was stirred overnight at room temperature. The resulting precipitate was filtered, washed with ether and dried under vacuum to yield 3-(1-aza-2-amino-1-cycloheptene)benzoic acid (4.9 g).

EXAMPLE C 3-(1-aza-2-amino-1-cycloheptene)-5-trifluoromethylbenzoic acid hydrochloride

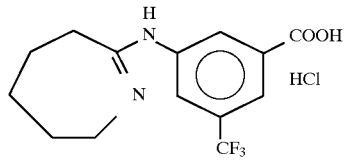

The title compound was synthesized according to the methodology of Example B, substituting an equivalent amount of 3-amino-5-trifluoromethyl benzoic acid [which was synthesized by reduction of 3-nitro-5-trifluoromethyl benzoic acid (Lancaster) in ethanol with 10% Pd/C under 50 psi H₂ for 4 hours] for 3-aminobenzoic acid.

EXAMPLE D 3-guanidino-5-trifluoromethylbenzoic acid, hydrochloride

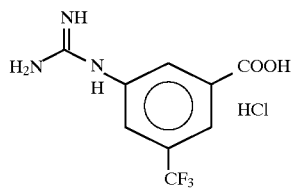

The title compound was synthesized according to the methodology of Example A, substituting an equivalent amount of 3-amino-5-trifluoromethylbenzoic acid (see Example C) for 3-aminobenzoic acid.

EXAMPLE E

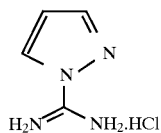

The above compound was prepared according to Bernatowicz, JOC, Vol. 57, No. 8, (1992), p. 2497–2502. NMR was consistent with the proposed structure.

EXAMPLE F

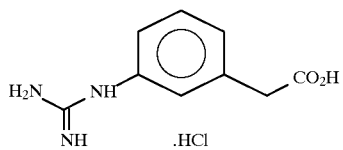

A solution of 3-aminophenylacetic acid (2.712 g, 17.9 mmol), the compound of Example E (3.023 g, 20.6 mmol), and Hunig's base (3.6 mL, 20.6 mmol) in dioxane (30 mL)/water (15 mL) was refluxed for 16 hours under argon. Upon heating, a white precipitate formed. The reaction was cooled to room temperature and the white solid filtered off. The solid was washed with 1:1 dioxane/water (3×5 mL). The solid was suspended in 15 mL of water and acidified with concentrated HCl until the solid dissolved. The solution was concentrated in vacuo and the resulting yellow residue slurried with ether. The yellow solid was collected by vacuum filtration (3.025 g, 74% yield). NMR was consistent with the proposed structure.

EXAMPLE G

Step A

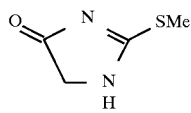

To a mixture of 2-thiohydantoin (5.5 g, 47.4 mmol) in absolute ethanol (60 mL) was added methyl iodide (3.5 mL, 56.6 mmol). The mixture was heated at reflux for 5 hours. The mixture was cooled to room temperature and concentrated in vacuo and the crude product used directly in the next step.

Step B

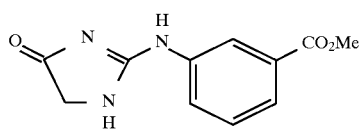

To a mixture of the thiomethyl starting material from Step A (1.0 g, 3.8 mmol) in absolute ethanol (20 mL) was added ethyl 3-aminobenzoate (2.5 g, 15.3 mmol). The mixture was stirred at room temperature for 16 hours. The mixture was concentrated in vacuo and the residue chromatographed (85:14:1 CH₂Cl₂:MeOH:NH₄OH) to give the desired product (414 mg, 44%).

Step C

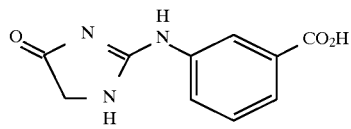

To a mixture of the ester from Step B (250 mg, 1.0 mmol) in THF (2 mL) and methanol (2 mL) was added 1.0N NaOH sol. (2 mL). The reaction solution was stirred at room temperature for 2 hours and concentrated in vacuo. The residue was suspended in water and carefully acidified to pH 4 with 1N HCl. The solid was collected by filtration and washed with water and ether to give the desired product (190 mg, 87%).

EXAMPLE 1

Synthesis of ethyl 2-[4-[[[3-[(aminoiminomethyl)amino]phenyl]carbonyl]amino]phenyl] cyclopropanecarboxylate, monohydrate trifluoroacetate salt

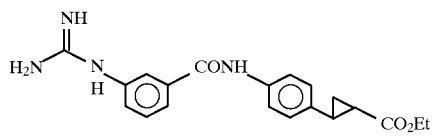

Step A

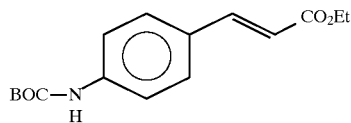

A mixture of ethyl 4-aminocinnamate (2 g, 10.45 mmol), di-tertbutyl dicarbonate (2.5 g, 11.5 mmol) and potassium carbonate (4.3 g, 31.4 mmol) in THF/H$_2$O (1:1 36 mL) was stirred at room temperature overnight. The solution was concentrated and the residue was dissolved in ethyl acetate. The solution was washed successively with water, 1N HCl and brine, dried over Na$_2$SO$_4$, filtered and concentrated in vacuo to give 1.2 g of the desired compound as yellow solid.

Step B

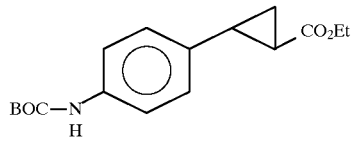

To the compound of Step A (1.2 g, 4.12 mmol) and Pd(OAc)$_2$ (10 mg) in ether (20 mL) an etheral CH$_2$N$_2$ solution (30 mL, prepared from 2.1 g N-nitroso-N-methyl urea) was added slowly at 0° C. The reaction mixture was warmed to room temperature, stirred for 3 hours and then glacial acetic acid (2 mL) was added to remove the excess CH$_2$N$_2$. The reaction mixture was washed successively with water, saturated sodium bicarbonate and brine, dried over Na$_2$SO$_4$ and evaporated to afford 1.2 g of a black oil.

Step C

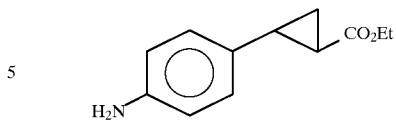

The compound of Step B (1.2 g, 3.9 mmol) was dissolved in methylene chloride (6 mL) and the resulting solution cooled to 0° C. in an ice bath. To the reaction mixture was added trifluoroacetic acid (2 mL). After 15 minutes the ice bath was removed and the reaction stirred for 3 hours. The reaction mixture was concentrated the residue treated with 5% aqueous K$_2$CO$_3$, and extracted with ethyl acetate (3×). The combined organic phases were washed with water and brine, dried over Na$_2$SO$_4$ and evaporated. The crude product was purified by flash chromatography on silica gel, eluting with 1% MeOH/CH$_2$Cl$_2$ to give 550 mg of the desired pure compound as a brown solid.

Step D

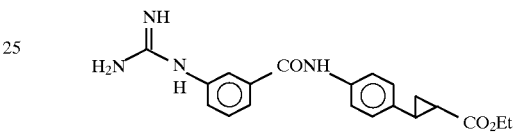

To a stirred solution of the compound of Example A (526 mg, 2.4 mmol) in dimethyl formamide (10 mL) at 0° C. was added 1-methylpiperidine (238 mg, 2.4 mmol) followed by the addition of isobutyl chloroformate (328 mg, 2.4 mmol). After 5 minutes the compound of Step C (492 mg, 2.4 mmol) in dimethyl formamide (1 mL) was introduced. The reaction mixture was warmed to room temperature and stirred overnight. The solvent was removed under reduced pressure, and the residue was purified by reverse phase HPLC-Method 1 to give 300 mg yellow oil.

Analysis Calculated for C$_{20}$H$_{22}$N$_4$O$_3$.1.5 TFA.1 H$_2$O: C, 49.73; H, 4.63; N, 10.09. Found: C, 49.74; H, 4.50; N, 10.29.

EXAMPLE 2

Synthesis of 2-[4-[[[3-[(aminoiminomethyl)amino]phenyl]carbonyl]amino]phenyl] cyclopropanecarboxylic acid, trifluoroacetate salt

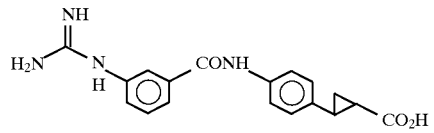

The product of Example 1 (220 mg, 0.6) was dissolved in methanol (2 mL) at room temperature. Lithium hydroxide (1M, 1 mL) was added and the reaction mixture was stirred overnight. The solution was concentrated and purified by reverse phase HPLC-Method 1 to give 120 mg of a yellow solid.

Analysis Calculated for C$_{18}$H$_{18}$N$_4$O$_3$.1.0 TFA.0.2 H$_2$O: C, 52.68; H, 4.29; N, 12.29. Found: C, 52.64; H, 3.93; N, 12.31.

The following compounds were synthesized using methodology and conditions similar to the methodology disclosed above.

EXAMPLE 3

2-[3-[[[[3-[(aminoiminomethyl)amino]phenyl] carbonyl]amino]methyl]phenyl] cyclopropanecarboxylic acid, trifluoroacetate salt

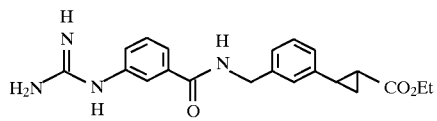

Anal. calc'd for $C_{18}H_{18}N_4O_3 \cdot 1$ TFA $\cdot 0.2$ H$_2$O: C, 52.68; H, 4.29; N, 12.29 Found: C, 52.64; H, 3.93; N, 12.31.

EXAMPLE 4 ethyl 2-[4-[[[3-[(aminoiminomethyl)amino]phenyl] carbonyl]amino]-2-methoxyphenyl] cyclopropanecarboxylate, trifluoroacetate salt, monohydrate

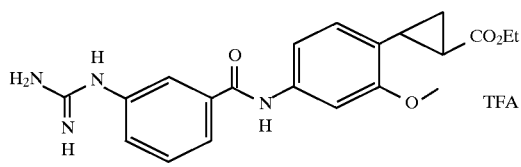

Anal. calc'd for $C_{21}H_{24}N_4O_4 \cdot 1$ TFA$\cdot 1$ H$_2$O: C, 52.27; H, 5.15; N, 10.60 Found: C, 52.28; H, 4.97; N, 10.54.

EXAMPLE 5

2-[4-[[[3-[(aminoiminomethyl)amino]phenyl] carbonyl]amino]-2-methoxyphenyl] cyclopropanecarboxylic acid, trifluoroacetate salt

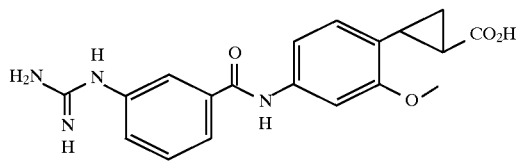

Anal. calc'd for $C_{19}H_{20}N_4O_4 \cdot 1.5$ TFA: C, 48.99; H, 4.02; N, 10.39. Found: C, 48.89; H, 4.18; N, 10.34.

EXAMPLE 6

2-[4-[[[3-[(aminoiminomethyl)amino]-5-(trifluoromethyl)phenyl]carbonyl]amino]phenyl] cyclopropanecarboxylic acid, trifluoroacetate salt

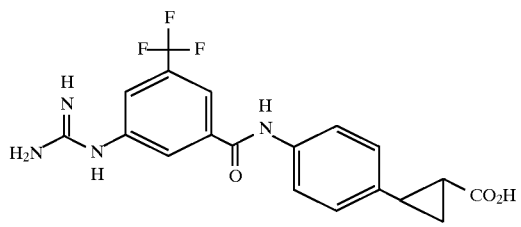

Step A

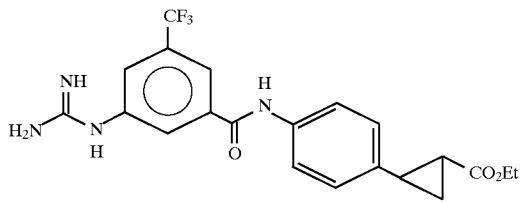

The above compound was prepared in the same manner as described in Example 1 replacing the compound of Example A used in Step D with the compound of Example D.

Step B

The compound of Step A was hydrolyzed in the same manner as described in Example 2 to produce the title compound.

Analysis Calculated for $C_{19}H_{17}N_4O_3F_3 \cdot 1.3$ TFA: C, 46.78; H, 3.30; N, 10.10. Found: C, 46.45; H, 3.46; N, 10.11.

EXAMPLE 7

2-[4-[[[3-[(1,4,5,6-tetrahydropyrimidin-2-yl)amino] phenyl]carbonyl]amino]phenyl] cyclopropanecarboxylic acid, trifluoroacetate salt

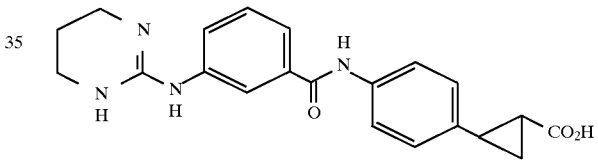

Step A

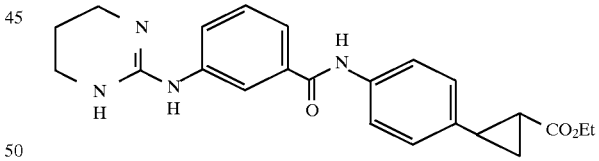

The above compound was prepared following the procedure described in Example 1, Step D, replacing the compound of Example A with 3-(3-[(1,4,5,6-tetrahydropyrimidin-2-yl)amino]benzoic acid. NMR was consistent with the proposed structure.

Step B

The compound of Step A was hydrolyzed in the same manner as described in Example 2 to produce the title compound.

Anal. calc'd for $C_{21}H_{22}N_4O_3 \cdot 1.1$TFA$+0.6$ H$_2$O: C, 54.14; H, 4.76; N, 10.89 Found: C, 54.29; H, 4.98; N, 10.53.

EXAMPLE 8

2-[4-[[[3-[(amino[(aminocarbonyl)imino]methyl]amino]phenyl]carbonyl]amino]phenyl] cyclopropanecarboxylic acid, trifluoroacetate salt

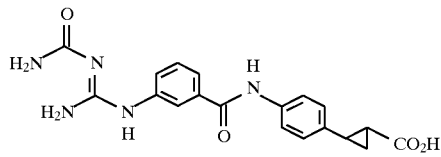

Step A

Preparation of methyl 3-[[(cyanoimino)(methylthio)methyl]amino]benzoate

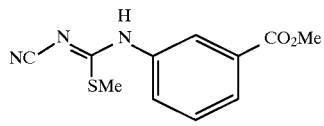

A stirred mixture of 3-amino methyl benzoate (6.04 g, 40 mmol) and dimethyl N-cyanodithioiminocarbonate (11.96 g, 80 mmol) in pyridine (70 ml) was heated at reflux under a nitrogen atmosphere for 2.5 hours. The reaction mixture was cooled to room temperature. On standing overnight at room temperature the above compound crystallized from the reaction mixture affording 6.2 g (two crops). The compound was used without further purification in the proceeding examples.

NMR was consistent with the proposed structure.

Step B

Preparation of methyl 3-[[amino(cyanoimino)methyl]amino]benzoate

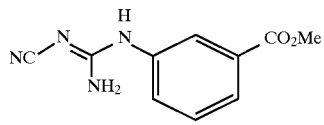

A mixture of the compound produced in Step A (1.0 g) and ammonium hydroxide (2 ml) in ethanol (20 ml) was heated at 70° C. in a sealed tube for 3.5 hours. The reaction mixture was cooled to room temperature and reduced to half its volume. After standing overnight at room temperature a white solid was obtained, which was isolated by filtration and washed with methanol. This afforded the above compound (389 mg) as a white solid.

NMR was consistent with the proposed structure.

Step C

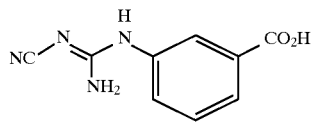

To a stirred solution of the compound produced in Step B (2.9 g, 13.3 mmol) in THF (15 ml) and methanol (15 ml), 1N NaOH (14 ml) was added. The reaction mixture was stirred at room temperature for 2 hours and concentrated in vacuo to afford a white solid. The residue was acidified by suspension in water followed by addition of 1N HCl. The resultant solid was filtered, washed with diethyl ether, and dried to afford the above compound (2.4 g).

NMR was consistent with the proposed structure.

Step D

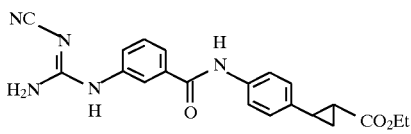

The above compound was prepared following the procedure described in Example 1, Step D, replacing the compound of Example A with the compound produced in Step C. NMR was consistent with the proposed structure.

Step E

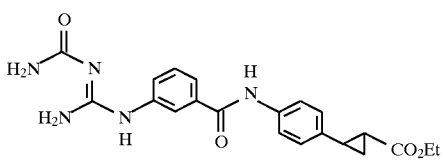

To a stirred solution of the compound produced in Step D (0.23 g, 0.58 mmol) in $CH_2Cl_2$ (4 ml) was added TFA (4 ml). The reaction mixture was stirred at 25° C. for 2 hours. The reaction mixture was concentrated in vacuo to afford a brown oil. NMR was consistent with the proposed structure.

Step F

To a stirred solution of the compound produced in Step E (0.23 g, 0.58 mmol) in MeOH (4 ml), 1N sodium hydroxide was added (2 ml). The reaction mixture was stirred at room temperature overnight. The reaction was concentrated in vacuo and the residue purified by reverse phase HPLC (eluent, water/acetonitrile/trifluoroacetic acid) to give the title compound as a white solid (178 mg).

Anal. calc'd for $C_{19}H_{19}N_5O_4 \cdot 1.2$ TFA: C, 49.60; H, 3.93; N, 13.51 Found: C, 49.85; H, 3.69; N, 13.75.

EXAMPLE 9

2-[4-[[[3-[(aminoiminomethyl)amino]phenyl]carbonyl]amino]-3-fluorophenyl] cyclopropanecarboxylic acid, trifluoroacetate salt

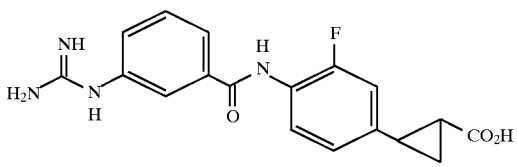

Step A

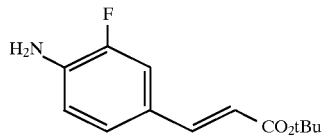

A solution of 4-bromo-2-fluoroaniline (10 g, 52.6 mmol), t-butylacrylate (8.2 g, 65.8 mmol), tri-o-tolylphosphine (1.28 g, 4.2 mmol), triethylamine (5.32 g, 52.6 mmol) and palladium (II) acetate was heated in a pressure tube at 100° C. for 2 hours. The reaction mixture was filtered through celite, and the filtrate was partitioned between diethyl ether and water. The diethyl ether extracts were separated, combined, dried ($Na_2SO_4$) and concentrated in vacuo to afford the crude product (15 g). The crude product was chromatographed (silica gel, 20% ethyl acetate/hexane) to afford the pure product (4.9 g) as an orange oil. NMR was consistent with the proposed structure.

Step B

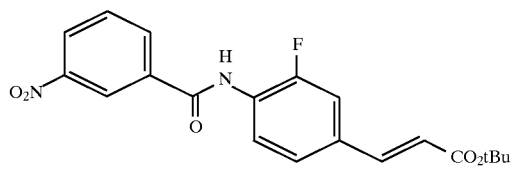

To a stirred solution of 3-nitrobenzoyl chloride (473 mg, 2.55 mmol) and the compound produced in Step A (0.6 g, 2.55 mmol) in methylene chloride (13 ml) at 0° C., triethylamine (258 mg, 2.55 mmol) was added dropwise. The reaction mixture was allowed to warm to room temperature and stirred for 2 hours. The reaction mixture was quenched with water and then partitioned between diethyl ether and water. The ether layer was separated, dried ($Na_2SO_4$) and evaporated to afford the crude product. The crude product was chromatographed (silica gel, 30% ethyl acetate/hexane) to afford the pure product (660 mg, 67%). NMR was consistent with the proposed structure.

Step C

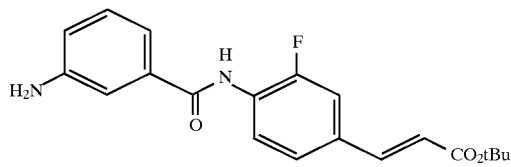

To a stirred solution of the compound produced in Step B (660 mg, 1.71 mmol) in ethanol (10 ml) at 75° C., tin (II) chloride dehydrate (1.54 g, 6.88 mmol) was added in one portion. The reaction mixture was maintained at 75° C. for 30 minutes, allowed to cool to room temperature and quenched with solid sodium hydrogen carbonate until effervescence ceased. The crude reaction mixture was partitioned between water and ethyl acetate. The organic layer was separated, dried ($Na_2SO_4$) and evaporated to afford the crude product. The crude product was chromatographed (silica gel, methylene chloride/methanol/ammonium hydroxide; 98/1/1) to afford the pure product (450 mg). NMR was consistent with the proposed structure.

Step D

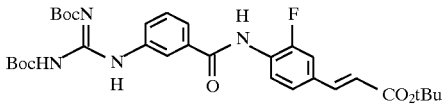

To a stirred solution of the compound produced in Step C (350 mg, 0.98 mmol) and N,N'-bisboc thiourea (216 mg, 0.98 mmol) in dimethyl formamide (0.29 ml) at 0° C., mercury (II) chloride (293 mg, 1.1 mmol) was added in one portion. The reaction mixture was stirred at 0° C. for 30 minutes, filtered through celite and the filtrate evaporated in vacuo to afford the crude product. The crude product was chromatographed (silica gel, 20% ethyl acetate/hexane) to afford the desired product (400 mg) as a white solid. NMR was consistent with the proposed structure.

Step E

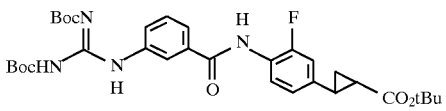

To a stirred solution of the compound produced in Step D (350 mg, 0.58 mmol) and palladium (II) acetate (30 mg, 0.32 eq) in diethyl ether (5 ml) at 0° C. was added an ethereal solution of diazomethane (excess). The reaction mixture was allowed to attain room temperature over approximately 2 hours and then evaporated overnight under a stream of nitrogen. The crude product was chromatographed (silica gel, 20% ethyl acetate/hexane) to afford the desired product (230 mg). NMR was consistent with the proposed structure.

Step F

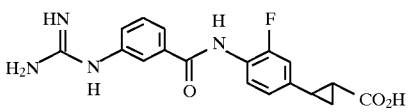

To a stirred solution of the compound produced in Step E (230 mg) in methylene chloride (3 ml) was added trifluoroacetic acid (3 ml). The reaction mixture was stirred at room temperature for 16 hours and evaporated to afford the crude product. The crude product was purified using reverse phase HPLC (eluent, water/acetonitrile/trifluoroacetic acid) to afford the title compound (100 mg).

Anal. calc'd for $C_{18}H_{17}N_4O_3 \cdot 1.05$ TFA: C, 50.71; H, 3.82; N, 11.77 Found: C, 50.61; H, 3.66; N, 11.60.

The activity of the compounds of the present invention was tested in the following assays. The results of testing in the assays are tabulated in Table 1.

VITRONECTIN ADHESION ASSAY

Materials

Human vitronectin receptor($\alpha_v\beta_3$) was purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.,* 266(3):1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay was essentially the same as previously reported [Niiya et al., *Blood,* 70:475–483 (1987)]. The purified human vitronectin receptor ($\alpha_v\beta_3$) was diluted from stock solutions to 1.0 $\mu$g/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 $\mu$L/well (100 ng receptor/well). The plates were sealed and incubated overnight at 4° C. to allow the receptor to bind to the wells. All remaining steps were at room temperature. The assay plates were emptied and 200 $\mu$L of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 $\mu$L aliquots to the assay plate was carried out with a CETUS Propette robot; the final concentration of the labeled ligand was 1 nM and the highest concentration of test compound was $1.0\times10^{-4}$M. The competition occurred for two hours after which all wells were washed with a plate washer as before. Affinity purified horseradish peroxidase labeled goat anti-biotin antibody was diluted 1:3000 in $TBS^{+++}$/BSA and 125 $\mu$L were added to each well. After 30 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm [Rodbard et al., *Int. Atomic Energy Agency, Vienna,* pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

PURIFIED IIb/IIIa RECEPTOR ASSAY

Materials

Human fibrinogen receptor ($\alpha_{IIb}\beta_3$) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor ($\alpha_{IIb}\beta_3$) was diluted from stock solutions to 1.0 $\mu$g/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 $\mu$L/well (100 ng receptor/well). The plates were sealed and incubated overnight at 4° C. to allow the receptor to bind to the wells. All remaining steps were at room temperature. The assay plates were emptied and 200 $\mu$L of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 $\mu$L aliquots to the assay plate was carried out with a CETUS Propette robot; the final concentration of the labeled ligand was 1 nM and the highest concentration of test compound was $1.0\times10^{-4}$M. The competition occurred for two hours after which all wells were washed with a plate washer as before. Affinity purified horseradish peroxidase labeled goat anti-biotin antibody was diluted 1:3000 in $TBS^{+++}$/BSA and 125 $\mu$L were added to each well. After 30 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., *Int. Atomic Energy Agency, Vienna,* pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $α_vβ_3$ antagonist ($IC_{50}$ in the range 3–10 nM) was included on each plate as a positive control.

TABLE 1

| Example | AVB3 IC50 (nM) | IIb/IIIa IC50 (nM) |
|---|---|---|
| 1 | 525 | 3650 |
| 2 | 30.5 | 533 |
| 3 | 923 | 5280 |
| 5 | 81.1 | 2890 |
| 6 | 122 | 9700 |
| 7 | 19.0 | 4800 |
| 8 | 1380 | 13100 |

What is claimed is:
1. A compound of the formula

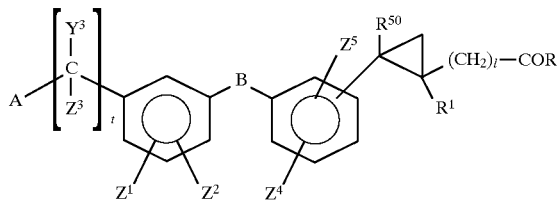

or a pharmaceutically acceptable salt thereof, wherein
A is

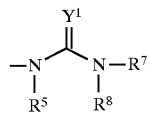

wherein $Y^1$ is selected from the group consisting of N—$R^2$, O, and S;
$R^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy and phenyl;
or $R^2$ taken together with $R^7$ forms a 5 membered heteroaromatic ring;
or $R^2$ taken together with $R^7$ forms a 5 membered heteroaromatic ring fused with a phenyl group;
$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above;
or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;
$R^5$ is selected from the group consisting of H, alkyl, alkenyl, alkynyl, benzyl, and phenethyl; or A is

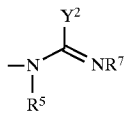

wherein $Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—$R^9$ and —O—$R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above;

or $Y^2$ (when $Y^2$ is carbon) taken together with $R^7$ forms a 4–12 membered mononitrogen containing ring optionally substituted with alkyl, aryl or hydroxy;

$Z^1$, $Z^2$, $Z^4$ and $Z^5$ are independently selected from the group consisting of H; alkyl; hydroxy; alkoxy; aryloxy; arylalkyloxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of

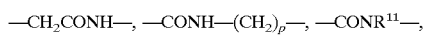
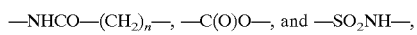

wherein p is an integer selected from the group consisting of 0, 1 and 2; wherein $R^{11}$ is selected from the group consisting of H, alkyl, alkenyl, alkynyl, benzyl and phenethyl; wherein n is an integer selected from the group consisting of 0, 1, 2 and 3;

l is an integer 0, 1, 2, or 3;

t is an integer 0, 1 or 2;

$R^{50}$ is selected from the group consisting of H, alkyl and aryl;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof;

$Y^3$ and $Z^3$ are independently selected from the group consisting of H, alkyl, aryl, cycloalkyl and aralkyl;

$R^1$ is selected from the group consisting of hydrogen; alkyl; amino,

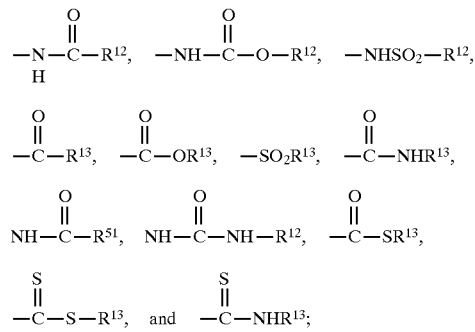

$R^{12}$ is selected from the group consisting of H, alkyl, cycloalkyl, alkylaryl and aryl;

$R^{51}$ is selected from the group consisting of N-substituted pyrrolidinyl, piperidinyl and morpholinyl;

$R^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido; alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

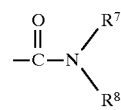

wherein $R^7$ and $R^8$ are as defined above and provided that taken together with the nitrogen, $R^7$ and $R^8$ comprise an amino acid.

2. A compound according to claim 1 wherein t is 0.

3. A compound according to claim 2 of the formula

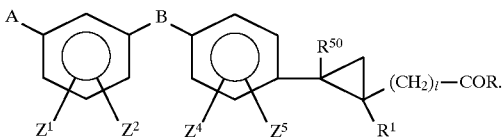

4. A compound according to claim 3 wherein l is 0.
5. A compound according to claim 4 wherein B is —CONH—(CH$_2$)$_p$— wherein p is 0 or 1.
6. A compound according to claim 5 wherein R$^{50}$ and R$^1$ are H.
7. A compound according to claim 6 wherein R is selected from the group consisting of hydroxy or alkoxy.
8. A compound according to claim 7 selected from the group consisting of ethyl 2-[4-[[[3-[(aminoiminomethyl)amino]phenyl]carbonyl]amino]phenyl]cyclopropanecarboxylate;

2-[4-[[[3-[(aminoiminomethyl)amino]phenyl]carbonyl]amino]phenyl]cyclopropanecarboxylic acid;

2-[3-[[[[3-[(aminoiminomethyl)amino]phenyl]carbonyl]amino]methyl]phenyl]cyclopropanecarboxylic acid;

ethyl 2-[4-[[[3-[(aminoiminomethyl)amino]phenyl]carbonyl]amino]-2-methoxyphenyl]cyclopropanecarboxylate;

2-[4-[[[3-[(aminoiminomethyl)amino]phenyl]carbonyl]amino]-2-methoxyphenyl]cyclopropanecarboxylic acid;

2-[4-[[[3-[(aminoiminomethyl)amino]-5-(trifluoromethyl)phenyl]carbonyl]amino]phenyl]cyclopropanecarboxylic acid;

2-[4-[[[3-[(1,4,5,6-tetrahydropyrimidin-2-yl)amino]phenyl]carbonyl]amino]phenyl]cyclopropanecarboxylic acid;

2-[4-[[[3-[(amino[(aminocarbonyl)imino]methyl]amino]phenyl]carbonyl]amino]phenyl]cyclopropanecarboxylic acid; and 2-[4-[[[3-[(aminoiminomethyl)amino]phenyl]carbonyl]amino]-3-fluorophenyl]cyclopropanecarboxylic acid.

9. A pharmaceutical composition comprising a therapeutically effective amount of a compound of the formula

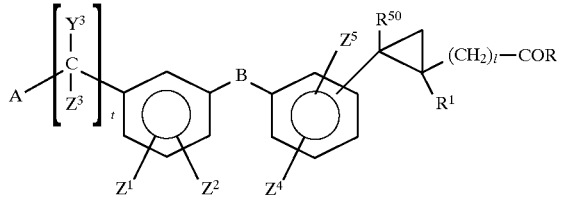

or a pharmaceutically acceptable salt thereof, wherein A is

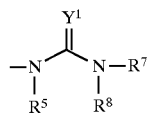

wherein Y$^1$ is selected from the group consisting of N—R$^2$, O, and S;

R$^2$ is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or R$^2$ taken together with R$^7$ forms a 4–12 membered dinitrogen containing heterocycle optionally substituted with one or more substituent selected from the group consisting of lower alkyl, hydroxy and phenyl;

or R$^2$ taken together with R$^7$ forms a 5 membered heteroaromatic ring;

or R$^2$ taken together with R$^7$ forms a 5 membered heteroaromatic ring fused with a phenyl group;

R$^7$ (when not taken together with R$^2$) and R$^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —SO$_2$R$^{10}$ wherein R$^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein $R^{10}$ is defined above;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl; or A is

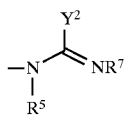

wherein $Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—$R^9$ and —O—$R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above;

or $Y^2$ (when $Y^2$ is carbon) taken together with $R^7$ forms a 4–12 membered mononitrogen containing ring optionally substituted with alkyl, aryl or hydroxy;

$Z^1$, $Z^2$, $Z^4$ and $Z^5$ are independently selected from the group consisting of H; alkyl; hydroxy; alkoxy; aryloxy; arylalkyloxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of

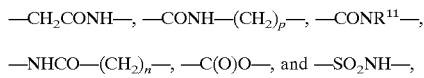

wherein p is an integer selected from the group consisting of 0, 1 and 2; wherein $R^{11}$ is selected from the group consisting of H, alkyl, alkenyl, alkynyl, benzyl and phenethyl; wherein n is an integer selected from the group consisting of 0, 1, 2 and 3;

l is an integer 0, 1, 2, or 3;

t is an integer 0, 1 or 2;

$R^{50}$ is selected from the group consisting of H, alkyl and aryl;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof;

$Y^3$ and $Z^3$ are independently selected from the group consisting of H, alkyl, aryl, cycloalkyl and aralkyl;

$R^1$ is selected from the group consisting of hydrogen; alkyl; amino,

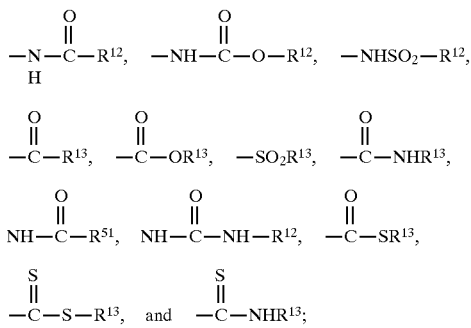

$R^{12}$ is selected from the group consisting of H, alkyl, cycloalkyl, alkylaryl and aryl;

$R^{51}$ is selected from the group consisting of N-substituted pyrrolidinyl, piperidinyl and morpholinyl;

$R^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

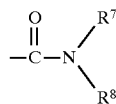

wherein R⁷ and R⁸ are as defined above and provided that taken together with the nitrogen, R⁷ and R⁸ comprise an amino acid;

and a pharmaceutically acceptable carrier.

10. A pharmaceutical composition according to claim 9 wherein t is 0.

11. A pharmaceutical composition according to claim 10 of the formula

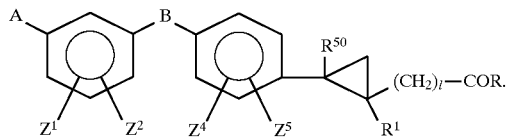

12. A pharmaceutical composition according to claim 11 wherein l is O.

13. A pharmaceutical composition according to claim 12 wherein B is —CONH—(CH₂)$_p$ wherein p is 0 or 1.

14. A pharmaceutical composition according to claim 13 wherein R⁵⁰ and R¹ are H.

15. A pharmaceutical composition according to claim 14 wherein the compound is selected from the group consisting of ethyl 2-[4-[[[3-[(aminoiminomethyl)amino]phenyl] carbonyl]amino]phenyl]cyclopropanecarboxylate;

2-[4-[[[3-[(aminoiminomethyl)amino]phenyl]carbonyl] amino]phenyl]cyclopropanecarboxylic acid;

2-[3-[[[[3-[(aminoiminomethyl)amino]phenyl]carbonyl] amino]methyl]phenyl]cyclopropanecarboxylic acid;

ethyl 2-[4-[[[3-[(aminoiminomethyl)amino]phenyl] carbonyl]amino]-2-methoxyphenyl] cyclopropanecarboxylate;

2-[4-[[[3-[(aminoiminomethyl)amino]phenyl]carbonyl] amino]-2-methoxyphenyl]cyclopropanecarboxylic acid;

2-[4-[[[3-[(aminoiminomethyl)amino]-5-(trifluoromethyl)phenyl]carbonyl]amino]phenyl] cyclopropanecarboxylic acid;

2-[4-[[[3-[(1,4,5,6-tetrahydropyrimidin-2-yl)amino] phenyl]carbonyl]amino]phenyl] cyclopropanecarboxylic acid;

2-[4-[[[3-[(amino[(aminocarbonyl)imino]methyl]amino] phenyl]carbonyl]amino]phenyl] cyclopropanecarboxylic acid; and 2-[4-[[[3-[(aminoiminomethyl)amino]phenyl]carbonyl] amino]-3-fluorophenyl]cyclopropanecarboxylic acid.

16. A method for treating conditions mediated by the α$_v$β$_3$ integrin in a mammal in need of such treatment comprising administering an effective α$_v$β$_3$ inhibiting amount of a compound of the formula

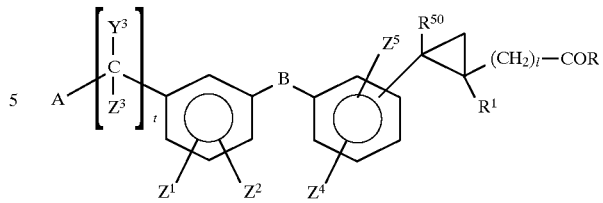

or a pharmaceutically acceptable salt thereof, wherein A is

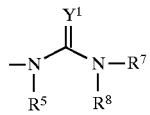

wherein Y¹ is selected from the group consisting of N—R², O, and S;

R² is selected from the group consisting of H; alkyl; aryl; hydroxy; alkoxy; cyano; nitro; amino; aminocarbonyl; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or R² taken together with R⁷ forms a 4–12 membered dinitrogen containing heterocycle optionally substituted with one or more substituent selected from the group consisting of lower alkyl, hydroxy and phenyl;

or R² taken together with R⁷ forms a 5 membered heteroaromatic ring;

or R² taken together with R⁷ forms a 5 membered heteroaromatic ring fused with a phenyl group;

R⁷ (when not taken together with R²) and R⁸ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —SO$_2$R$^{10}$ wherein R$^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

wherein R$^{10}$ is defined above;

or NR$^7$ and R$^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

R$^5$ is selected from the group consisting of H, alkyl, alkenyl, alkynyl, benzyl, and phenethyl; or A is

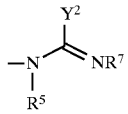

wherein Y$^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; —S—R$^9$ and —O—R$^9$ wherein R$^9$ is selected from the group consisting of H; alkyl; aralkyl; aryl; alkenyl; and alkynyl; or R$^9$ taken together with R$^7$ forms a 4–12 membered mononitrogen containing sulfur or oxygen containing heterocyclic ring; and R$^5$ and R$^7$ are as defined above;

or Y$^2$ (when Y$^2$ is carbon) taken together with R$^7$ forms a 4–12 membered mononitrogen containing ring optionally substituted with alkyl, aryl or hydroxy;

Z$^1$, Z$^2$, Z$^4$ and Z$^5$ are independently selected from the group consisting of H; alkyl; hydroxy; alkoxy; aryloxy; arylalkyloxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

B is selected from the group consisting of

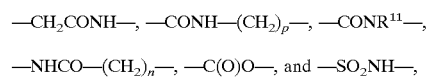

wherein p is an integer selected from the group consisting of 0, 1 and 2; wherein R$^{11}$ is selected from the group consisting of H, alkyl, alkenyl, alkynyl, benzyl and phenethyl; wherein n is an integer selected from the group consisting of 0, 1, 2 and 3;

l is an integer 0, 1, 2, or 3;

t is an integer 0, 1 or 2;

R$^{50}$ is selected from the group consisting of H, alkyl and aryl;

R is X—R$^3$ wherein X is selected from the group consisting of O, S and NR$^4$, wherein R$^3$ and R$^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof;

Y$^3$ and Z$^3$ are independently selected from the group consisting of H, alkyl, aryl, cycloalkyl and aralkyl;

R$^1$ is selected from the group consisting of hydrogen; alkyl; amino,

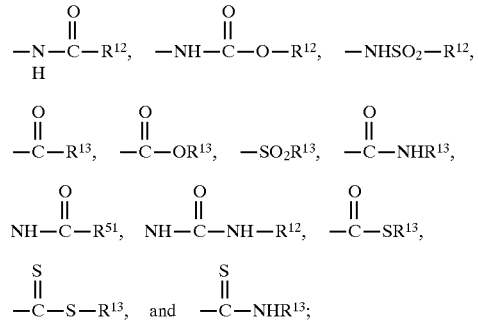

R$^{12}$ is selected from the group consisting of H, alkyl, cycloalkyl, alkylaryl and aryl;

R$^{51}$ is selected from the group consisting of N-substituted pyrrolidinyl, piperidinyl and morpholinyl;

R$^{13}$ is selected from the group consisting of hydrogen; alkyl; alkenyl; alkynyl; aryl; carboxyl derivatives; haloalkyl; monocyclic heterocycles; monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido;

alkyl optionally substituted with halo, haloalkyl, hydroxy, alkoxy, aryloxy, thio, alkylthio, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, haloalkyl, cyano, nitro, hydroxy, carboxyl derivatives, alkoxy, aryloxy, amino, alkylamino, dialkylamino, amido, aryl, fused aryl, monocyclic heterocycles; and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl;

aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, carboxyl derivatives, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles; and

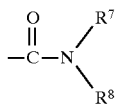

wherein $R^7$ and $R^8$ are as defined above and provided that taken together with the nitrogen, $R^7$ and $R^8$ comprise an amino acid.

17. The method according to claim 16 wherein the compound is selected from the group consisting of
ethyl 2-[4-[[[3-[(aminoiminomethyl)amino]phenyl]carbonyl]amino]phenyl]cyclopropanecarboxylate;
2-[4-[[[3-[(aminoiminomethyl)amino]phenyl]carbonyl]amino]phenyl]cyclopropanecarboxylic acid;
2-[3-[[[[3-[(aminoiminomethyl)amino]phenyl]carbonyl]amino]methyl]phenyl]cyclopropanecarboxylic acid;
ethyl 2-[4-[[[3-[(aminoiminomethyl)amino]phenyl]carbonyl]amino]-2-methoxyphenyl]cyclopropanecarboxylate;
2-[4-[[[3-[(aminoiminomethyl)amino]phenyl]carbonyl]amino]-2-methoxyphenyl]cyclopropanecarboxylic acid;
2-[4-[[[3-[(aminoiminomethyl)amino]-5-(trifluoromethyl)phenyl]carbonyl]amino]phenyl]cyclopropanecarboxylic acid;
2-[4-[[[3-[(1,4,5,6-tetrahydropyrimidin-2-yl)amino]phenyl]carbonyl]amino]phenyl]cyclopropanecarboxylic acid;
2-[4-[[[3-[(amino[(aminocarbonyl)imino]methyl]amino]phenyl]carbonyl]amino]phenyl]cyclopropanecarboxylic acid; and
2-[4-[[[3-[(aminoiminomethyl)amino]phenyl]carbonyl]amino]-3-fluorophenyl]cyclopropanecarboxylic acid.

18. The method according to claim 16 wherein the condition treated is tumor metastasis.

19. The method according to claim 17 wherein the condition treated is tumor metastasis.

20. The method according to claim 16 wherein the condition treated is solid tumor growth.

21. The method according to claim 17 wherein the condition treated is solid tumor growth.

22. The method according to claim 16 wherein the condition treated is angiogenesis.

23. The method according to claim 17 wherein the condition treated is angiogenesis.

24. The method according to claim 16 wherein the condition treated is osteoporosis.

25. The method according to claim 17 wherein the condition treated is osteoporosis.

26. The method according to claim 16 wherein the condition treated is humoral hypercalcemia of malignancy.

27. The method according to claim 17 wherein the condition treated is humoral hypercalcemia of malignancy.

28. The method according to claim 16 wherein the condition treated is smooth muscle cell migration.

29. The method according to claim 17 wherein the condition treated is smooth muscle cell migration.

30. The method according to claim 16 wherein restenosis is inhibited.

31. The method according to claim 17 wherein restenosis is inhibited.

* * * * *